United States Patent [19]
Clark et al.

[11] Patent Number: 5,194,133
[45] Date of Patent: Mar. 16, 1993

[54] SENSOR DEVICES

[75] Inventors: Michael G. Clark, Buckinghamshire; Rosemary A. Lee, Middlesex; Christopher R. Lowe, Essex; Philip Maynard, Cambridgeshire; Rajinder S. Sethi, Northampton; Donald J. Weir, London, all of England

[73] Assignee: The General Electric Company, p.l.c., England

[21] Appl. No.: 695,429

[22] Filed: May 3, 1991

[30] Foreign Application Priority Data

May 4, 1990 [GB] United Kingdom ............... 9010072

[51] Int. Cl.$^5$ .............. G01N 27/26; G01N 27/30; G01N 27/447; B01D 57/02
[52] U.S. Cl. .............. 204/299 R; 204/182.8; 204/182.9; 204/403; 204/406; 204/412
[58] Field of Search ............. 204/403, 412, 411, 409, 204/406, 299 R, 182.8, 182.9

[56] References Cited

U.S. PATENT DOCUMENTS

| | | | |
|---|---|---|---|
| 4,409,088 | 11/1983 | Kanno et al. | 204/409 X |
| 4,786,394 | 11/1988 | Enzer et al. | 204/409 X |
| 4,831,442 | 10/1989 | Yamaguchi et al. | 204/416 X |
| 4,891,120 | 1/1990 | Setti et al. | 204/299 R |

FOREIGN PATENT DOCUMENTS

| | | |
|---|---|---|
| 0078590 | 5/1983 | European Pat. Off. . |
| 0126426 | 11/1984 | European Pat. Off. . |
| 0299778 | 1/1989 | European Pat. Off. . |
| 0311377 | 4/1989 | European Pat. Off. . |
| 59-178353 | 10/1980 | Japan .................. 204/411 |
| 2191110 | 12/1987 | United Kingdom . |

OTHER PUBLICATIONS

Chemical Abstract CA 108(24):215569b; Vanini, G. M. et al., "Neat and admixed mesomorphic polysiloxane otationary phases for open-tubular column gas chromatography" Anal. Chem. 60(11), 1119-24.
Ma, T. S. & Hassan, S. S. M. "Organic Analysis Using Ion-Selective Electrodes, vol. 1 Methods" pp. 109-113.
Chemical Abstract CA115(4):40799; Laeubli, Markus W. "Simultaneous determination of alkali and alkaline earth metal ions with isocratic ion chromatography using the Super-Sep cation column (according to Schomburg)", Recent Dev. Exch. 2 [Proc. Int. Conf. Ion Exch. Process], 2nd, 31-9.

Primary Examiner—John Niebling
Assistant Examiner—John S. Starsiek, Jr.
Attorney, Agent, or Firm—Kirschstein, Ottinger, Israel & Schiffmiller

[57] ABSTRACT

A sensor device for the analysis of a sample fluid comprises a substrate in a surface of which an elongate channel is micromachined. The channel contains a material, such as a starch, agarose, alginate, carrageenin or polyacrylic polymer gel, with a biological material for causing separation of the sample fluid as the fluid passes along the channel. The biological material may comprise, for example, a binding protein, an antibody, a lectin, an enzyme, a sequence of enzymes or a lipid. Pairs of sensing electrodes are spaced apart along the walls of the channel. The device may be used, for example, for testing blood samples.

24 Claims, 5 Drawing Sheets

SENSOR DEVICES

BACKGROUND OF THE INVENTION

1. Field of the Invention

This invention relates to sensor devices, and particularly, but not exclusively, to sensors for use in clinical analysis.

2. Description of Related Art

There is an increasing demand for analytical information in sectors including health care and veterinary medicine, and in the food, pharmaceutical, bioprocessing, agrochemical and petrochemical industries. This information is at present mainly provided by sophisticated centralised analytical laboratories. Such laboratories are both capital and labour intensive, and there is evidence that they are unlikely to meet the needs of the future. For example, in human health care, speed in both the detection and monitoring of key metabolites is essential for the correct diagnosis and subsequent treatment of diseases, and this requires the provision of local, fast analysis.

The need to perform analysis in a non-laboratory environment requires new diagnostic techniques in order to provide real-time information on the levels of key substances such as gases, ions, metabolites, drug, proteins and hormones. Unequivocal diagnosis will usually depend on the simultaneous determination of several key metabolites, as would be required, for example, for the diagnosis and management of diabetes, kidney, liver and thyroid dysfunction, bone disorders and cardiovascular disease. Furthermore, such determination could also prove valuable in blood and tissue typing and in screening for pregnancy complications, fertility, drug abuse, neonatal disorder, infectious diseases, rheumatic disorders and drug overdoses.

A sensor device for such purposes should preferably be small and easily portable and should not require complex prior preparation of the sample, such as blood, to be tested.

SUMMARY OF THE INVENTION

It is an object of the present invention to provide an improved sensor device.

According to the invention there is provided a sensor device for analysis of a sample fluid, the device comprising a substrate; at least one elongate channel micromachined in a surface of the substrate and containing a material to cause separation of said sample fluid as the fluid passes along the channel; and a plurality of sensing electrode pairs spaced apart along the channel, the electrodes of each pair being located opposite each other at opposed side walls of the channel.

If necessary, a cover will be provided over the or each channel for retaining the fluid in the channel.

Preferably the material to cause separation comprises a gel to which is attached a biological material and with which the or each channel is packed. The gel may be, for example, a carbohydrate e.g. starch, agarose, alginate, carrageenin, a polyacrylic polymer, or an inorganic gel. The channel walls may be coated with a biological substance, such as an enzyme. The material to cause separation is chosen to have different affinity for different components of the sample fluid, and may, for example, be a liquid crystal polymer or an ionisable polymer, according to the nature of the sample fluid. Alternatively, the material to cause separation may be a binding protein, antibody, lectin, enzyme or sequence of enzymes, lipid or any other chemical which interacts selectively and reversibly with the substance which is to be separated.

BRIEF DESCRIPTION OF THE DRAWINGS

Embodiments of the invention will now be described, by way of example, with reference to the accompanying drawings, in which.

DETAILED DESCRIPTION OF THE PREFERRED EMBODIMENTS

Figure 1:
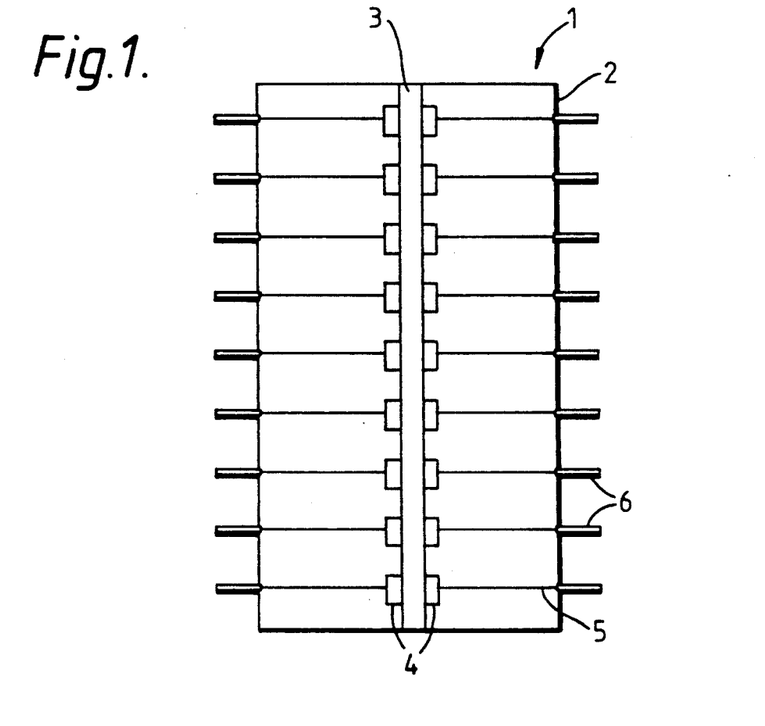
FIG. 1 is a schematic plan view of a first form of sensor device in accordance with the invention.

Referring to FIG. 1 of the drawings, a sensor device 1 comprises a substrate 2 in which an elongate groove 3 is formed by a micromachining process. The substrate may be formed of glass, ceramic or silicon, on which is deposited or grown a layer of dielectric material, such as silicon dioxide. The micromachining process may comprise chemical or physical etching of the substrate.

The width of the groove 3 may be in a range of, say, 10–500 $\mu$m, and is preferably about 100 $\mu$m. Its depth may be 50 $\mu$m or more and its length will preferably be greater than 1 mm.

Figure 2:
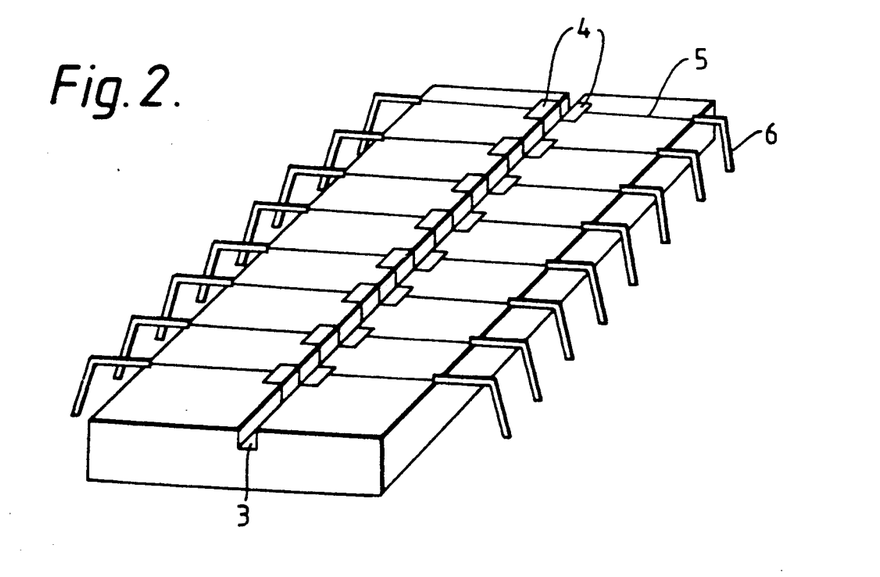
FIG. 2 is a schematic pictorial view of the device of FIG. 1.

Electrode pairs 4 are deposited on the substrate so that part of each electrode extends down the side wall of the groove 3, the electrodes of each pair lying on opposite sides of the groove. The electrode pairs are equally spaced along the length of the groove. The electrodes are preferably formed of a corrosion-resistant material, such as gold, platinum or iridium, and are deposited by any suitable deposition process, such as sputtering. The walls of the groove may be previously recessed at the electrode positions, so that the electrodes lie flush with the groove walls in order not to impede the flow of a liquid sample through the groove.

Conductors 5 are deposited across the substrate surface to connect the electrodes to respective contact pins 6. The contact pins may turn downwards as shown, so that the device may be plugged into a standard dual-in-line integrated circuit holder. Alternatively, the electrodes may be connected to contact pads on the surface of the substrate.

Figure 3:
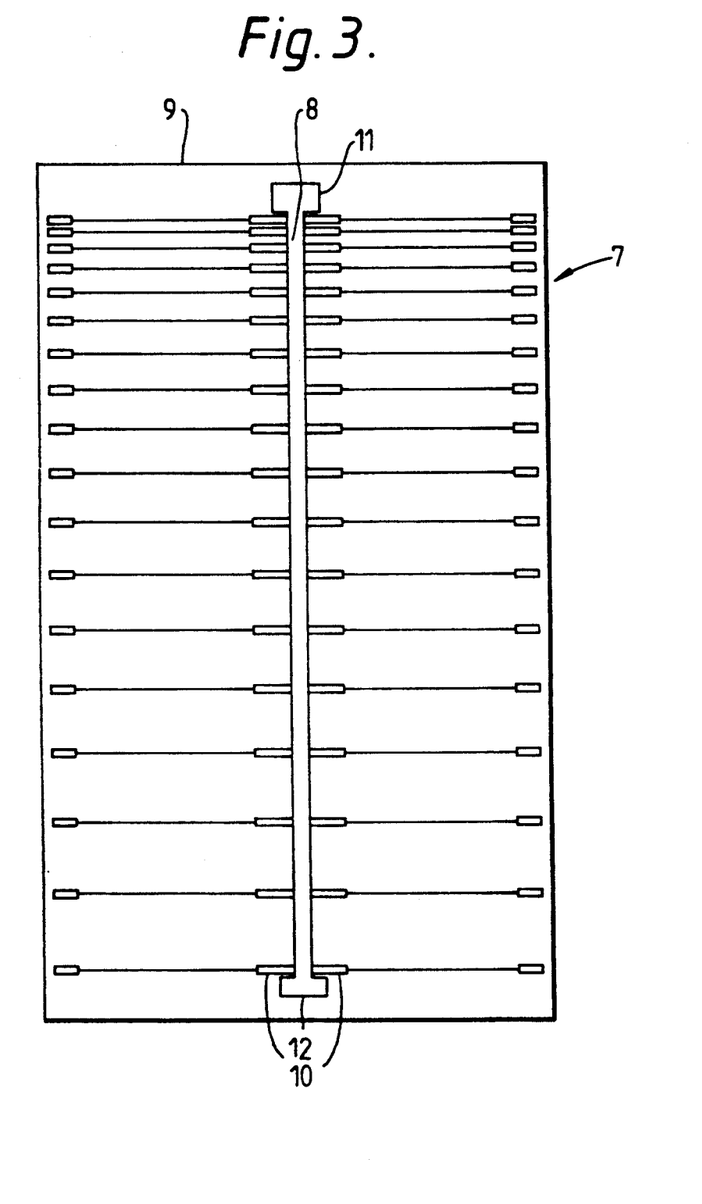
FIG. 3 is a schematic plan view of a second form of sensor device in accordance with the invention.

FIG. 3 is a schematic plan view of an alternative form of sensor device 7. A groove 8 is formed in a substrate 9, and electrode pairs 10 are provided at the groove walls as before. However, in this case the electrodes are not equidistantly spaced along the length of the groove. In order to achieve a maximum number of measurement positions and a configuration more in keeping with the expected progress of the separation function of the groove, successive electrode pairs are spaced apart at distances of 1 unit, 2 units, 3 units, 4 units, and so on. If desired, the contact pins or pads could be equally spaced along the substrate to facilitate their connection to the monitoring circuitry.

Wells 11 and 12 are provided at opposite ends of the groove 8 to facilitate the introduction of the sample fluid into the groove and its collection after passing along the groove. Electrodes are preferably provided in the wells for electrophoresis purposes.

Figure 4:
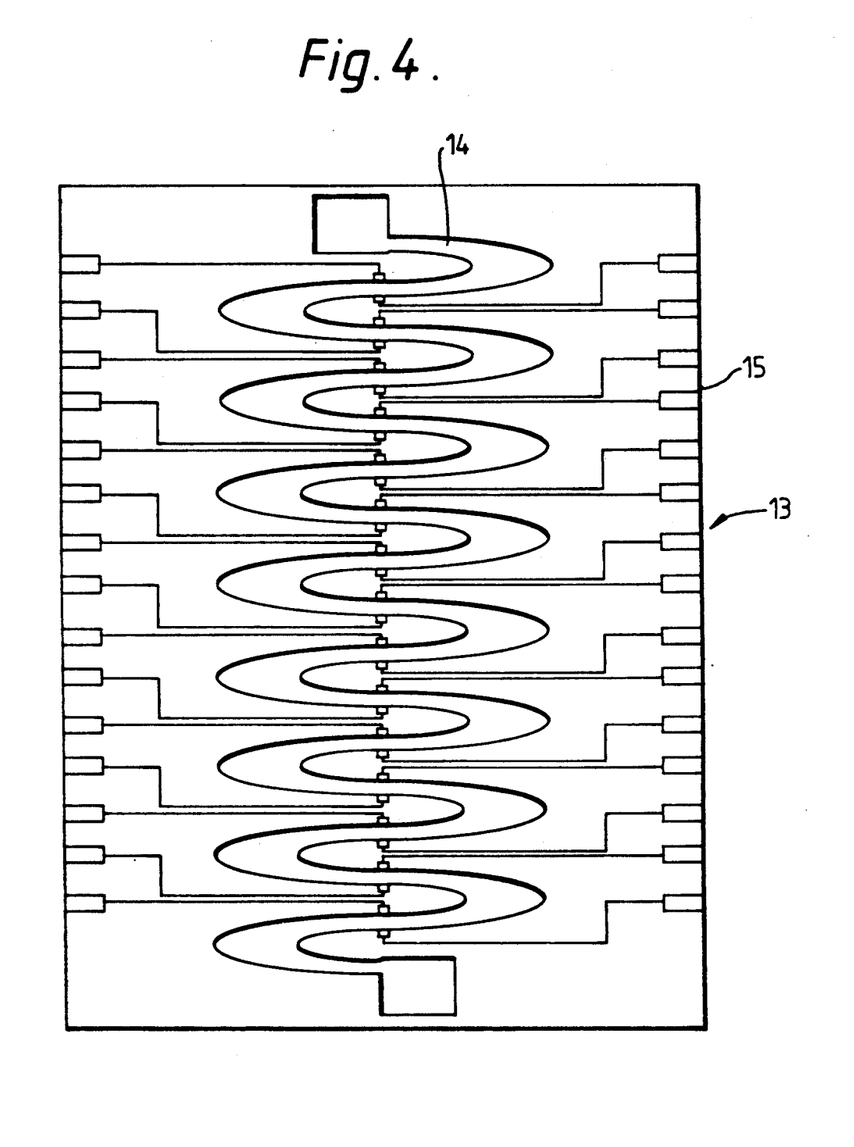
FIG. 4 is a schematic plan view of a third form of sensor device in accordance with the invention.

FIG. 4 shows an alternative configuration of sensor device 13 in which a groove 14 is formed in serpentine fashion in a substrate 15. This appreciably increases the length of the groove. The electrode pairs may be equally spaced or unequally spaced along the length of the groove. Wells are provided at the ends of the groove.

Figure 5:
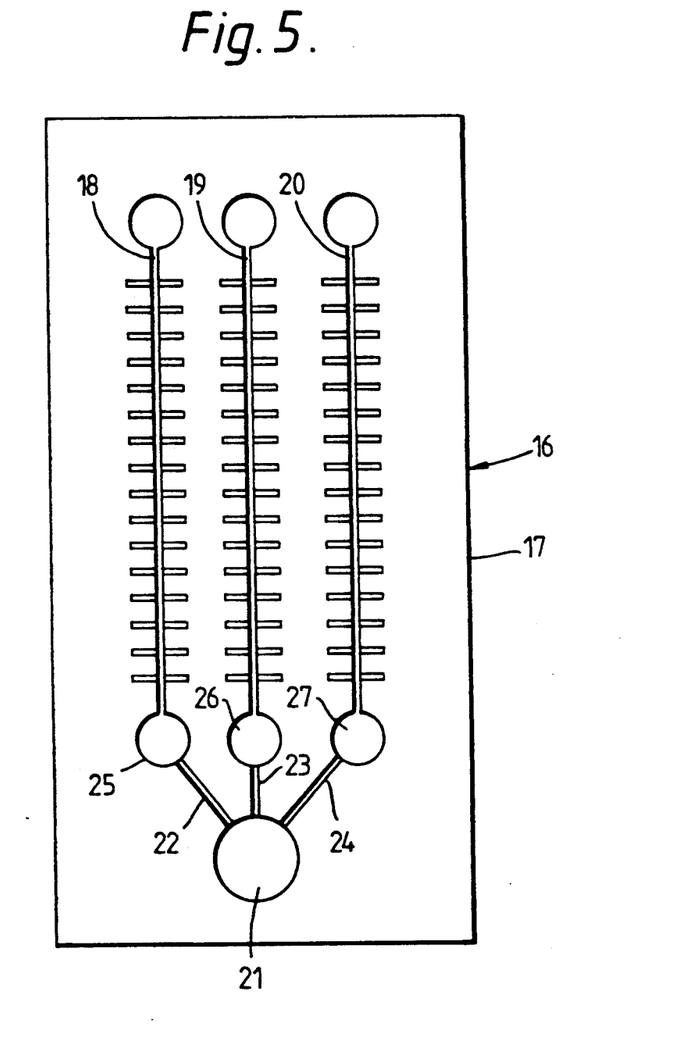
FIG. 5 is a schematic plan view of a fourth form of sensor device in accordance with the invention.

Referring to FIG. 5, in another alternative configuration a sensor device 16 comprises a substrate 17 in which three parallel grooves 18-20 are formed and associated electrode pairs are provided. A well 21 formed in the substrate for receiving a sample fluid is common to the three grooves 18-20. The well 21 is connected by grooves 22, 23 and 24, respectively, to wells 25, 26 and 27 with which the ends of the grooves 18, 19 and 20, respectively, communicate. The wells 25-27 are provided to receive an enzyme material, as will be explained later. Wells 28, 29 and 30 are provided near the other end of the substrate 17 to receive sample fluid after it has flowed through the grooves 18, 19 and 20, respectively. This arrangement allows two sample fluids and a reference fluid to be derived from the fluid fed into the well 21 and to flow through the device simultaneously. Alternatively, the grooves may be used for simultaneous measurement of a number of different indicating chemicals. The device may alternatively have any other required number of parallel grooves. For example, six grooves might be used for measurement, respectively, of levels of potassium, sodium, creatimine, urea, $Cl^-$ and $HCO_3$ in a blood sample, as would be required for the diagnosis of kidney disease.

In each of the above-described embodiments the grooves are filled with a substance which causes them to act as chromatographic separating columns. The grooves contain a biological material, such as a binding protein, antibody, lectin, enzyme or sequence of enzymes, lipid or any other chemical which interacts selectively and reversibly with the substance which is to be separated. The grooves may be lined with the material, or the grooves may be packed with a gel to which the material is attached. The gel may be, for example, a carbohydrate e.g. starch, agarose, alginate, carrageenin, a polyacrylic polymer, or an inorganic gel. Alternatively, the electrodes may be amperometric enzyme electrodes deposited by micro-fabrication techniques.

If the sample fluid is a liquid or, more particularly, a gas containing different anisometric molecules, an appropriate chromatographic substance is a liquid crystal polymer in which the liquid crystal forming molecules are attached as side-chains to the polymer by flexible spacers. The sensor is then preferably operated in the temperature range within which the polymer is in a liquid crystal phase, although separation is improved by use of a liquid crystal polymer even in its isotropic phase. One example of a class of liquid crystal polymers suitable for use in the present invention is the mesomorphic polysiloxane (MEPSIL) polymers described by G. M. Janini, R. J. Lamb, J. H. Purnell and O. S. Tyagi in their article "Physicochemical Studies and Analytical Applications of Mesomorphic Polysiloxane (MEPSIL) Solvents by Gas-Liquid Chromatography" published as Chapter 14 in "Side Chain Liquid Crystal Polymers" (edited by C. B. McArdle; Blackie, 1989). Separations using liquid crystalline chromatographic substances show particularly good resolution because the interactions between molecules in the sample and the liquid crystal side chains are very dependent on geometrical shape. Liquid crystals are therefore particularly suited to separating geometrical isomers or other very similar pairs of molecules.

The most appropriate method of ionic species resolution is exploitation of ion chromatography. This technique is a special version of high performance ion exchange chromatography by which ionic and ionizable solutes can be separated by differences in the electrostatic interaction with an ionizable stationary phase. The detection of the ionic species separated chromatographically is achieved using the pairs of electrodes configured as a conductivity device.

Any of a number of types of stationary phase may be inserted into the microgrooves in order to make them effective in resolving isocratically a mixture of mono- and divalent cations and anions. Such phases include (i) Polystyrene-divinylbenzene (PS-DVB). Chemical modification of the polymer allows preparation of anion or cation exchange stationary phases with excellent pH stability in the range 0–14.

(ii) Silica-based ion exchange phases. Silanised silica or polymer-coated silica are effective phase media for ion chromatography. For example, a layer of the co-polymer polybutadiene-maleic acid (PBDMA) deposited on the walls of the groove or grooves in various thicknesses and then cross-linked by a peroxide initiated radical chain reaction via the in-chain double bonds yields an insoluble film capable of serving as a stationary phase for ion chromatography.

(iii) Silica-bonded macrocycles. The attachment of macrocycles such as the crown ethers to silica makes possible the design of systems capable of the selective and quantative removal of cations from aqueous solutions. Immobilisation of 18-crown-6 to the silica walls of the groove at an appropriate ligand density should permit isocratic separation of the complementary cations. Isocratic separation is a type of chromatography in which all solutes are separated by their affinity for a solid phase with a fixed running phase.

(iv) Natural carboxylic polyether antibiotics. The carboxylic polyethers are a class of antibiotics produced by various Streptomyces species containing heterocyclic rings and a variety of functional oxygen atoms of the carbonyl, carboxyl, ether, hydroxyl and ketone types. Such compounds are capable of forming selective complexes with alkali-metal and alkaline earth metal cations. Hence, the carboxyl ethers ionomycin, lasalocid, monensin, nigericin and salinomycin may be covalently bonded to silica and used for the resolution of complementary ions.

(v) Electrosynthesised chromatographic stationary phases. Electrochemical synthesis of ion chromatography stationary phases has a number of distinct advantages over the above procedures; thus, it permits a rapid and easy column preparation, easy modification of the stationary phase, production of a reproducible physical and chemically stable polymer and accurate control of stationary phase thickness and composition. Polypyrrole, incorporating various polymeric counter-anions such as CM-dextran, dextran-sulphate heparin, gelatin or alginate may prove particularly effective since it could be deposited in a controlled fashion between the pairs of electrodes. Similarly, polypyrrole-immobilised polyether antibiotics or macrocycles could prove an effective alternative.

The two principal metabolites required for a kidney function test device as mentioned above are urea and creatinine. Both metabolites will be hydrolised to $NH_4+$ using their respective hydrolases, urease and creatininase.

whence the liberated $NH_4+$ will be estimated by ion chromatography on PBDMA-coated silica or one of the alternatives listed in (i-v) above. Enzymes will be chemically cross-linked in the sample wells of FIGS. 3 and 4, in the enzyme wells 25-27 of FIG. 5 or between the pairs of electrodes via entrapment in electrochemically deposited polypyrrole. Alternatively, a small "slug" of electrochemically deposited enzyme could be deposited midway down the length of the groove such that the first half of the groove monitors the background conductance whilst the urea level is monitored by the increased steady state conductance level as the sample continuously passes through the enzyme "slug".

In operation of the above-described devices, a liquid, such as blood, which is to be analysed is fed into one end of the groove or grooves and is separated into its components by the substances contained in the grooves. The components are then analysed as they pass the electrodes on the groove wall.

The microfabrication techniques may alternatively be used to fabricate microseparation structures based on capillary chromatography, electrophoresis or iso-electric focussing. Miniature fluid handling and metering devices, pumps and valves may also be provided on the substrate by similar techniques. The devices may also include a micromachined structure to feed a filtered predetermined amount of sample fluid into the groove or grooves.

Figure 6:
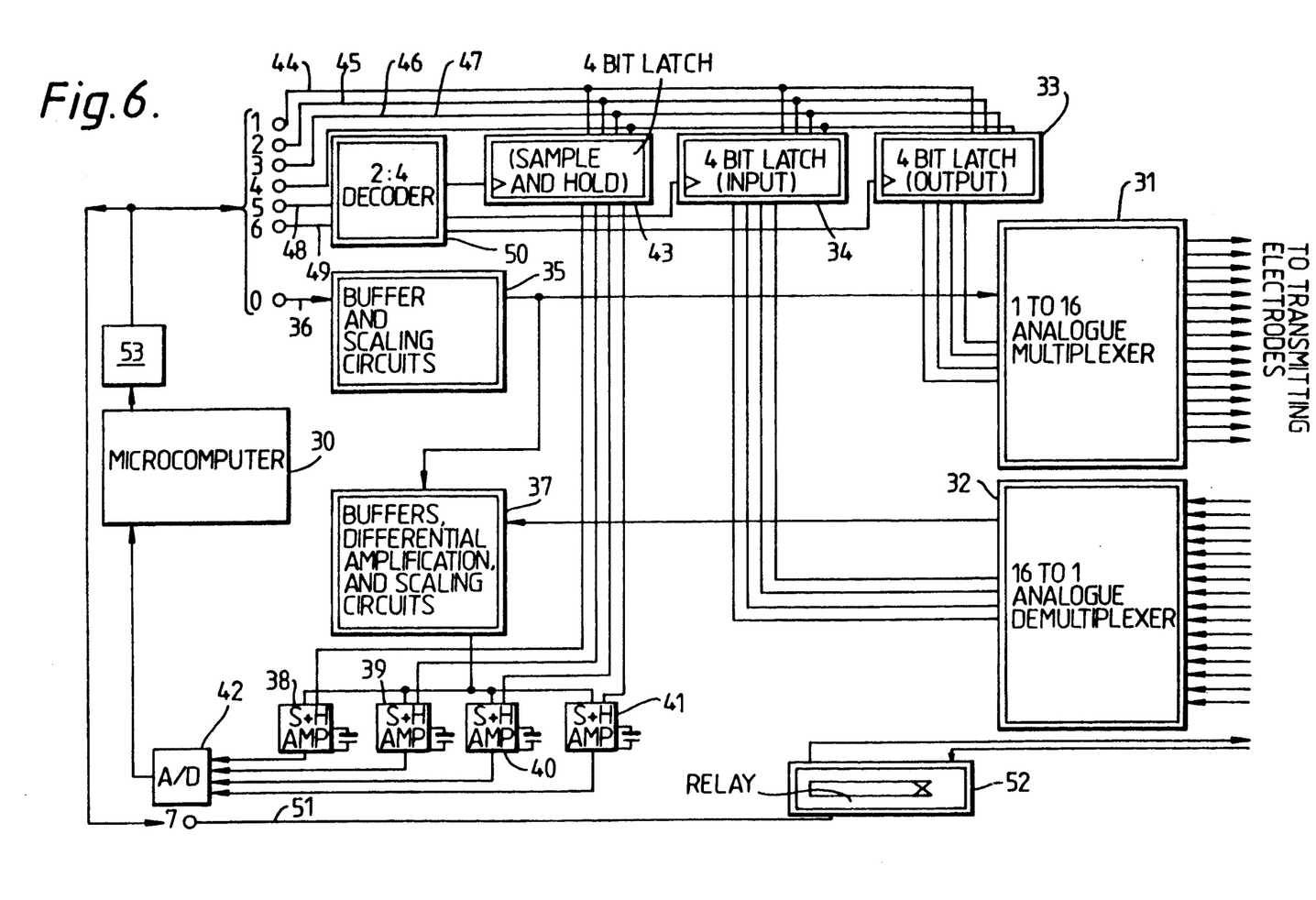
FIG. 6 is a schematic block diagram of circuitry for processing the outputs of the sensor devices.

FIG. 6 of the drawings is a schematic block diagram of circuitry for processing the outputs from the sensor electrodes. The sensors have a multiplicity of electrodes, for example sixteen on each side of the groove, and it is necessary to read the impedance between all the electrodes on one side of a groove and all the electrodes on the other side in less than 10 seconds. The processing system must therefore be capable of switching rapidly between electrodes, without causing any electrochemical effects.

This rapid switching is accomplished by using a microcomputer 30 to control a set of analogue switches. The signal applied to a selected transmitting electrode on one side of the groove is a reactangular dc pulse, 800 mV high and 120 $\mu$s wide. The signal received by the selected receiving electrode on the other side of the groove is an attenuated version of the applied pulse, and the degree of attenuation will be determined by the conductivity of the media between the selected electrodes. The media conductivity has many components, and these are to be studied, but other variables involved in conductivity measurements such as surface area of the electrodes and distance between them remains constant. The received signal differs in appearance from the applied signal in that it will be reduced in total height and the waveform will be rounded off due to capacitive effects at the electrode surfaces. In order to produce a detailed analysis of the received signal, sample and hold circuitry is used such that data can be captured at time intervals (20 $\mu$s) from this signal.

The signals are fed to the selected transmitted electrodes via an analogue multiplexer 31, and the signals from the receiving electrodes are fed back to the microcomputer via an analogue demultiplexer 32. The selection of the transmitting electrodes is effected digitally by a 4-bit output latch 33 and the selection of the receiving electrodes is effected by a 4-bit input latch 34. The signal pulse train is fed to the multiplexer 31 via a buffer and scaling circuit 35. The pulse train is obtained from the 0 bit of an 8-bit computer control byte over a line 36. The signals from the receiving electrodes are fed from the demultiplexer 32 to the microcomputer via buffer, differential amplification and scaling circuitry 37, sample and hold circuits 38-41 and an A/D converter 42. The signal from each receiving electrode is subtracted from the transmitted signal in the circuitry 37. The difference signal is amplified and is fed to the sample and hold circuits. The instant of sampling is controlled by a 4-bit latch 43.

The other bits of the 8-bit control byte are operative as follows. Bits 1, 2, 3 and 4, on lines 44-47, respectively, control the selection processes at the latches 33, 34 and 43. Bits 5 and 6 on lines 48 and 49 are fed to a 2:4 decoder 50 which determines which of the latches 33, 34 or 43 is to be operative at any instant. Bit 7 on a line 51 controls a relay 52 which applies a voltage from an external source to the electrodes in order to facilitate electrophoresis.

In operation of the system, the computer sends out, via an interface adaptor 53, the address of the selected transmitting electrode, as four bits, using bits 1 and 4 inclusive. The data are applied to the data latches 33, 34 and 43. Bits 5 and 6 carry the address of the output latch 33, which is selected by the decoder 50. The four bits selecting the transmitting electrode are thus transferred to the multiplexer 31.

The receiving electrode is then selected in the same manner, its 4-bit address being determined by bits 1-4, and is latched through the input latch 34 by decoding bits 5 and 6 in the decoder 50.

When the transmitting and receiving electrode pair has been selected, bit 0 goes high, and acts as the source of the signal to be applied to the transmitting electrode. Bits 5 and 6 are set such that they do not select any of the latches. The buffer and scaling circuit 35, consisting of simple operational amplifiers, reduces a 5 volt output signal applied from bit 0 to 800 mV and this is fed to the multiplexer 32 and thence to the selected electrode. The signal is also applied to the differential amplifier circuitry 37. The signal received by the selected receiving electrode passes through the demultiplexer 32 and is fed to the buffer, differential amplifier and scaling circuit 37 and then to the inputs of the four sample and hold circuits 38-41. (Bit 0 is still high at this point).

While the bit 0 is held high, one of the sample and hold circuits 38-41 is selected by setting the bits 1 to 4.

The sample and hold latch 43 is then selected by bits 5 and 6 to enable the latch, and thereby store the output from the analogue circuitry. This is repeated to capture the analogue data on the next sample and hold circuit. The sample and hold circuits may be enabled at, for example, 20 μsec intervals.

When all four sample and hold circuits 38-41 have data stored in them, the control byte is set to 0 (unless the relay 52 is enabled by the bit 7) thereby removing the applied analogue signal. The data from each sample and hold circuit is read into the four channels of the A/D converter 42. The next transmitting electrode can then be selected by repeating the steps described above.

As an example, let us assume that a signal is to be fed to the third transmitting electrode in the sequence and that a signal is to be received on the sixth receiving electrode. The codes to be produced by the microcomputer will be as set out in Table 1 below.

TABLE 1

| Control Byte Bit Number 7 6 5 4 3 2 1 0 | |
|---|---|
| 0 0 0 0 0 1 1 0 | Select third transmitter electrode |
| 0 0 1 0 0 1 1 0 | Send to multiplexer 31 by enabling output latch 33 (address 1) |
| 0 0 0 0 1 1 0 0 | Select sixth receiving electrode |
| 0 1 0 0 1 1 0 0 | Send to demultiplexer 32 by enabling input latch 34 (address 2) |
| 0 0 0 0 0 0 0 1 | Apply analogue signal to transmitter electrode |
| 0 0 0 0 0 0 1 1 | Select sample and hold circuit 38 |
| 0 1 1 0 0 0 1 1 | Enable from sample and hold latch 43 |
| 0 0 0 0 0 1 0 1 | Select sample and hold circuit 39 |
| 0 1 1 0 0 1 0 1 | latch as above |
| 0 0 0 0 0 1 1 1 | Select sample and hold circuit 40 |
| 0 1 1 0 0 1 1 1 | latch as above |
| 0 0 0 0 1 0 0 1 | Select sample and hold circuit 41 |
| 0 1 1 0 1 0 0 1 | latch as above |
| 0 0 0 0 0 0 0 0 | All off |
| 1 0 0 0 0 0 0 0 | Relay 52 on |

The circuitry described above has been designed to provide a measurement system capable of monitoring the bulk impedance of any media which may be found between the electrodes of a micro-electrode array. Conventional methods of measuring impedance in this type of environment require an alternating current source of very low voltage to be applied across a pair of electrodes which together with the separating media form one arm of a bridge circuit. In order to achieve steady readings, the bridge circuit automatically adjusts until balance is achieved. During this adjustment period, energy is continually applied to the measuring electrodes, inducing local heating due to the very small electrode area, and possibly causing some electrochemical effects. Switching electrodes in and out of a measurement system will cause local effects, changing the impedance measurement itself and increasing the length of time required by a bridge circuit to balance.

The measurement system described herein alleviates these problems associated with the conventional methods.

It would be possible to form the sensor devices described above as two identical micromachined substrates, which are then bonded together, face to face, to form an enclosed device. Alternatively, a cover plate might be bonded to any of the devices to cover the grooves.

We claim:

1. A sensor device for analysis of a sample fluid, the device comprising: a substrate having a surface; at least one elongate channel micromachined in the surface of the substrate for carrying said sample fluid, the channel having a length and opposed side walls; separation means, including a material in the channel, for causing separation of said sample fluid carried by the channel; a plurality of sensing electrode pairs spaced apart along the length of the channel, the electrodes of each pair being located opposite each other across the channel, and each electrode having a portion within the channel at one of said side walls; and means coupled to the electrodes for processing signals dependent upon conditions existing between the electrodes of each pair.

2. A device as claimed in claim 1, wherein the channel is packed with a gel; and wherein the material comprises a biological substance which is attached to the gel.

3. A device as claimed in claim 2, wherein the biological substance comprises a substance which interacts selectively and reversibly with the sample fluid.

4. A device as claimed in claim 3, wherein the biological substance is selected from the group consisting of a binding protein, an antibody, a lectin, an enzyme, a sequence of enzymes, and a lipid.

5. A device as claimed in claim 2, wherein the gel is selected from the group consisting of starch, agarose, alginate, carrageenin, a polyacrylic polymer and an inorganic gel.

6. A device as claimed in claim 1, wherein the walls of the channel are coated with a biological substance.

7. A device as claimed in claim 1, wherein the channel contains a body of a biological substance.

8. A device as claimed in claim 1, wherein the channel communicates with a well formed in the substrate and containing a biological substance.

9. A device as claimed in claim 1, wherein the material comprises a liquid crystal material.

10. A device as claimed in claim 9, wherein the liquid crystal material comprises a mesomorphic polysiloxane polymer.

11. A device as claimed in claim 1, wherein the material comprises polystyrene-divinylbenzene.

12. A device as claimed in claim 1, wherein the material comprises a silica-based ion exchange phase.

13. A device as claimed in claim 12, wherein the silica-based ion exchange phase is provided by depositing a layer of the co-polymer polybutadiene-malic acid on the walls of the channel and cross-linking said layer by a peroxide-initiated radical chain reaction.

14. A device as claimed in claim 1, wherein the material comprises a silica-bonded macrocycle.

15. A device as claimed in claim 14, wherein the macrocycle comprises a crown ether.

16. A device as claimed in claim 1, wherein the material comprises a carboxylic polyether antibiotic.

17. A device as claimed in claim 16, wherein the antibiotic is selected from the group consisting of ionomycin, lasalocid, monensin, nigericin and salinomycin, covalently bonded to silica.

18. A device as claimed in claim 1, wherein the material comprises an electrosynthesized chromatographic stationary phase.

19. A device as claimed in claim 1, wherein the channel is formed by one of a chemical and physical etching process.

20. A device as claimed in claim 1, wherein the resolution of components of the sample fluid is effected by one of capillary chromatography, electrophoresis, and iso-electric focussing.

21. A device as claimed in claim 1, wherein the substrate is formed from one of silicon, glass and ceramic.

22. A device as claimed in claim 1, wherein contact pins are connected to respective ones of the electrodes, the contact pins being configured for insertion into a dual-in-line integrated circuit holder.

23. A sensor device for analysis of a sample fluid, the device comprising: a substrate having a surface; at least one elongate channel micromachined in the surface of the substrate for carrying said sample fluid, the channel having a length and opposed side walls; separation means, including a material in the channel, for causing separation of said sample fluid carried by the channel; a plurality of sensing electrode pairs equally spaced apart along the length of the channel, the electrodes of each pair being located opposite each other on the opposed side walls of the channel; and means coupled to the electrodes for processing signals dependent upon conditions existing between the electrodes of each pair.

24. A sensor device for analysis of a sample fluid, the device comprising: a substrate having a surface; at least one elongate channel micromachined in the surface of the substrate for carrying said sample fluid the channel having a length, opposite ends and opposed side walls; separation means, including a material in the channel, for causing separation of said sample fluid carried by the channel; a plurality of sensing electrode pairs spaced apart along the length of the channel, the electrodes of each pair being located opposite each other on the opposed side walls of the channel, the spacing between adjacent electrode pairs increasing from one of said ends of the channel to the other of said ends; and means coupled to the electrodes for processing signals dependent upon conditions existing between the electrodes of each pair.

* * * * *